(12) United States Patent
Grunewald et al.

(10) Patent No.: US 11,058,485 B2
(45) Date of Patent: Jul. 13, 2021

(54) ABLATION TARGETING NERVES IN OR NEAR THE INFERIOR VENA CAVA AND/OR ABDOMINAL AORTA FOR TREATMENT OF HYPERTENSION

(71) Applicant: BIOSENSE WEBSTER (ISRAEL) LTD, Yokneam (IL)

(72) Inventors: Debby Grunewald, Los Angeles, CA (US); Kristine B. Fuimaono, Covina, CA (US); Tina Chan, El Monte, CA (US); Tom A. Ditter, Chino Hills, CA (US)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 89 days.

(21) Appl. No.: 16/601,544

(22) Filed: Oct. 14, 2019

(65) Prior Publication Data
US 2020/0038105 A1     Feb. 6, 2020

Related U.S. Application Data (62) Division of application No. 15/240,029, filed on Aug. 18, 2016, now Pat. No. 10,441,355, which is a
(Continued)

(51) Int. Cl.
*A61B 18/00* (2006.01)
*A61B 18/14* (2006.01)
(Continued)

(52) U.S. Cl.
CPC .......... *A61B 18/1492* (2013.01); *A61B 18/02* (2013.01); *A61B 18/0206* (2013.01);
(Continued)

(58) Field of Classification Search
USPC ............................................ 600/439; 606/41
See application file for complete search history.

(56) References Cited

U.S. PATENT DOCUMENTS

| 5,391,199 A | 2/1995 | Haim |
| 6,068,629 A | 5/2000 | Haissaguerre et al. |
| | (Continued) | |

FOREIGN PATENT DOCUMENTS

| AU | 2013205729 A1 | 11/2013 |
| CA | 2815317 A1 | 11/2013 |
| | (Continued) | |

OTHER PUBLICATIONS

Australian Patent Office Examination Report No. 1 for Application No. 2013205729, dated Feb. 22, 2017, 9 pages.
(Continued)

*Primary Examiner* — Nicole F Lavert
(74) *Attorney, Agent, or Firm* — Etan S. Chatlynne; Roberts Calderon Safran & Cole P.C.

(57) ABSTRACT

A method for the treatment of a patient for the purpose of lowering blood pressure and/or treating other medical conditions such as cardiac arrhythmias. A catheter having an ablation element is placed inside the body of a patient and is directed to a targeted location either on in the abdominal aorta where the right or left renal arteries branch from the aorta at or near the superior junction or ostia or on the inside of the inferior vena cava near the junction with the right renal vein or in the left renal vein at a position spatially near where the left renal artery branches from the abdominal aorta. Catheters designed for use in the method where these targeted locations are also disclosed and claimed.

15 Claims, 9 Drawing Sheets

Related U.S. Application Data division of application No. 13/827,114, filed on Mar. 14, 2013, now Pat. No. 9,439,722.

(60) Provisional application No. 61/644,724, filed on May 9, 2012.

(51) Int. Cl.

| | |
|---|---|
| *A61B 18/02* | (2006.01) |
| *A61B 18/18* | (2006.01) |
| *A61B 18/20* | (2006.01) |
| *A61M 25/09* | (2006.01) |
| *A61N 7/02* | (2006.01) |
| *A61B 17/22* | (2006.01) |
| *A61B 17/00* | (2006.01) |
| *A61M 25/01* | (2006.01) |

(52) U.S. Cl.
CPC .......... *A61B 18/18* (2013.01); *A61B 18/1815* (2013.01); *A61B 18/20* (2013.01); *A61M 25/09* (2013.01); *A61N 7/02* (2013.01); *A61B 17/22004* (2013.01); *A61B 2017/00318* (2013.01); *A61B 2018/0022* (2013.01); *A61B 2018/00285* (2013.01); *A61B 2018/00375* (2013.01); *A61B 2018/00404* (2013.01); *A61B 2018/00434* (2013.01); *A61B 2018/00505* (2013.01); *A61B 2018/00577* (2013.01); *A61B 2018/00791* (2013.01); *A61B 2018/00821* (2013.01); *A61B 2018/0212* (2013.01); *A61B 2018/1407* (2013.01); *A61B 2018/1435* (2013.01); *A61B 2018/1465* (2013.01); *A61B 2217/007* (2013.01); *A61B 2218/002* (2013.01); *A61M 2025/0183* (2013.01)

(56) References Cited

U.S. PATENT DOCUMENTS

| | | |
|---|---|---|
| 6,239,724 B1 | 5/2001 | Doron et al. |
| 6,292,695 B1 | 9/2001 | Webster, Jr. et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Haim et al. |
| 7,201,749 B2 | 4/2007 | Govari et al. |
| 7,729,742 B2 | 6/2010 | Govari |
| 8,768,470 B2 | 7/2014 | Deem et al. |
| 9,220,433 B2 | 12/2015 | Ditter et al. |
| 2002/0004644 A1 | 1/2002 | Koblish |
| 2002/0065455 A1 | 5/2002 | Ben-Haim et al. |
| 2002/0111618 A1 | 8/2002 | Stewart et al. |
| 2003/0018362 A1 | 1/2003 | Fellows et al. |
| 2003/0060820 A1* | 3/2003 | Maguire ................ A61B 18/00 606/41 |
| 2003/0120150 A1 | 6/2003 | Govari |
| 2004/0068178 A1 | 4/2004 | Govari |
| 2005/0288730 A1 | 12/2005 | Deem et al. |
| 2007/0029671 A1 | 2/2007 | Yamasaki |
| 2007/0083194 A1 | 4/2007 | Kunis et al. |
| 2007/0129720 A1 | 6/2007 | Demarais et al. |
| 2007/0129761 A1 | 6/2007 | Demarais et al. |
| 2008/0255642 A1 | 10/2008 | Zarins et al. |
| 2009/0312755 A1 | 12/2009 | Thapliyal et al. |
| 2010/0222851 A1 | 9/2010 | Deem et al. |
| 2011/0112400 A1* | 5/2011 | Emery ................ A61N 7/00 600/439 |
| 2011/0118726 A1* | 5/2011 | De La Rama ..... A61B 18/1492 606/33 |
| 2011/0257523 A1 | 10/2011 | Hastings et al. |
| 2011/0264086 A1* | 10/2011 | Ingle ................ A61B 18/1492 606/33 |
| 2012/0029505 A1 | 2/2012 | Jenson |
| 2012/0101413 A1 | 4/2012 | Beetel et al. |
| 2013/0006238 A1 | 1/2013 | Ditter et al. |
| 2013/0304047 A1 | 11/2013 | Grunewald et al. |

FOREIGN PATENT DOCUMENTS

| | | |
|---|---|---|
| CN | 1323180 A | 11/2001 |
| CN | 101309651 A | 11/2008 |
| CN | 103385754 A | 11/2013 |
| EP | 2204134 A1 | 7/2010 |
| EP | 2759275 A1 | 7/2014 |
| JP | H11262530 A | 9/1999 |
| JP | 2006504473 A | 2/2006 |
| JP | 2008515544 A | 5/2008 |
| JP | 2011136172 A | 7/2011 |
| JP | 2011224373 A | 11/2011 |
| JP | 2013233439 A | 11/2013 |
| RU | 2011131923 A | 2/2013 |
| RU | 2487686 C1 | 7/2013 |
| RU | 2013121593 A | 11/2014 |
| WO | 9605768 A1 | 2/1996 |
| WO | 0010475 A1 | 3/2000 |
| WO | 2004039273 A2 | 5/2004 |
| WO | 2010078175 A1 | 7/2010 |
| WO | 2010129661 A1 | 11/2010 |
| WO | 2011046880 A2 | 4/2011 |
| WO | 2011060339 A1 | 5/2011 |
| WO | 2012058434 A1 | 5/2012 |

OTHER PUBLICATIONS

Copending U.S. Appl. No. 13/174,742, filed Jun. 30, 2011, 53 pages (Biosense Webster (Israel)).
European Search Report for European Application No. 13167114, dated Nov. 22, 2013, 8 pages.
European Search Report for European Application No. 14160752.3, dated Jun. 30, 2014, 6 pages.
Office Action for Chinese Application No. 201310168279, dated Dec. 9, 2016, 3 pages.
Office Action for Chinese Application No. 201310168279, dated Mar. 22, 2017, 3 pages.
Office Action for Chinese Application No. 201310168279, dated May 5, 2016, 3 pages.
Office Action for European Application No. 13167114.1, dated Nov. 21, 2017, 3 pages.
Office Action for Japanese Application No. 2013098160, dated Jan. 31, 2017, 4 pages.
Partial European Search Report for European Application No. 13167114, dated Aug. 5, 2013, 5 pages.
Russian Examination Report issued in Application No. RU2013121593, dated Apr. 29, 2015, 2 pages.
Russian Examination Report issued in Application No. RU2013121593, dated May 4, 2016, 3 pages.
Russian Examination Report issued in Application No. RU2013121593, dated Sep. 18, 2013, 2 pages.

* cited by examiner

ABLATION TARGETING NERVES IN OR NEAR THE INFERIOR VENA CAVA AND/OR ABDOMINAL AORTA FOR TREATMENT OF HYPERTENSION

CROSS-REFERENCE TO RELATED APPLICATION

The present application is a Divisional Application under 35 U.S.C. § 121 of U.S. patent application Ser. No. 15/240,029, filed Aug. 18, 2016, which is a Divisional Application under 35 U.S.C. § 121 of U.S. patent application Ser. No. 13/827,114, filed Mar. 14, 2013, now U.S. Pat. No. 9,439,722, which claims priority under 35 U.S.C. § 119 to U.S. Provisional Patent Application No. 61/644,724, filed May 9, 2012. The entire contents of these applications are incorporated by reference herein in their entirety.

FIELD OF INVENTION

The present invention relates to a method and catheter for the treatment of hypertension and other medical conditions through targeted ablation of nerves associated with renal activity at specific targeted locations in or near the inferior vena cava and/or the abdominal aorta. Further, a specific catheter for use in the method is disclosed.

BACKGROUND OF INVENTION

RF electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical renal ablation procedure involves the insertion of a catheter having an electrode at its distal end into a renal artery in order to complete a circumferential lesion in the artery in order to denervate the artery for the treatment of hypertension. A reference electrode is provided, generally taped to the skin of the patient or by means of a second catheter. RF (radio frequency) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself.

Ablation of cardiac tissue using ultrasound energy, including High Intensity Focused Ultrasound (HIFU) energy has also been known for several years. In U.S. Pat. No. 7,201,749 entitled "Externally-applied high intensity focused ultrasound (HIFU) for pulmonary vein isolation" to Govari et al., an apparatus for the ablation of cardiac tissue is disclosed.

In U.S. Pat. No. 6,292,695 discloses a method of controlling cardiac fibrillation, tachycardia, or cardiac arrhythmia by the use of an electrophysiology catheter having a tip section that contains at least one stimulating electrode, the electrode being stably placed at a selected intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

The use of renal neurostimulation for the treatment of heart arrhythmias was disclosed in U.S. Patent Publication No. 2007/0129761 by Demarais et al. Demarais sets forth the use of neuromodulation to effectuate irreversible electroporation or electrofusion, ablation, necrosis and/or inducement of apoptosis, alteration of gene expression, action potential attenuation or blockade, changes in cytokine up-regulation and other conditions in target neural fibers. In some embodiments, such neuromodulation is achieved through application of neuromodulatory agents, thermal energy, or high intensity focused ultrasound.

In U.S. Patent Publication No. 2010/0222851, now U.S. Pat. No. 8,768,470, by Deem et al. the monitoring of renal neuromodulation was proposed stimulation to identify renal nerves to denervate or modulate. Stimulation of such nerves after prior to neural modulation would be expected to reduce blood flow while stimulation after neural modulation would not be expected to reduce blood flow to the same degree when utilizing similar situation parameters and locations prior to neural modulation.

SUMMARY OF THE INVENTION

The present invention is directed to a method for the treatment of patients, particularly, the treatment of hypertension and other associated medical conditions through the ablation of nerves associated with renal activity.

The present method for the treatment of a patient comprises the steps of inserting an ablation catheter having an ablation element mounted thereon into the body of a patient either to specific locations on the inside of the abdominal aorta or inside the inferior vena cava or left renal vein that target right and left renal nerves. Ablation at these specific targeted locations will denervate sufficient nerve fibers running through the renal arteries to the kidneys to treat hypertension or other medical conditions.

The method for the treatment of the patient includes the steps of inserting an ablation catheter into a body of a patient and ablating tissue at a targeted location wherein the targeted location is at or near the intersection of a renal artery and the abdominal aorta so as to denervate the renal artery. One targeted location is in the abdominal aorta in the vicinity of the superior junction of the abdominal aorta and the left renal artery. Another targeted location is in the abdominal aorta in the vicinity of the superior junction of the abdominal aorta and the right renal artery. Targeted locations include tissue in the abdominal aorta in the vicinity of the ostium of the abdominal aorta and the right renal artery and in the vicinity of the ostium of the abdominal aorta and the left renal artery.

A further method in accordance with the present invention calls for the treatment of a patient by inserting an ablation catheter into the inferior vena cava of a patient and, ablating tissue at a targeted location in the inferior vena cava in the vicinity of where the right renal vein branches off from the inferior vena cava so as to denervate the renal artery. The targeted location is in the vicinity of the ostium of the inferior vena cava and the right renal vein. This targeted location is, preferably, in the location spatially nearest to the superior junction between the right renal artery and the abdominal aorta.

Another method for the treatment of a patient in accordance with the present invention includes the steps of inserting an ablation catheter into the left renal vein of a patient and ablating tissue at a targeted location in the left renal vein where the left renal vein crosses over the junction where the left renal artery branches from the abdominal aorta so as to denervate the renal artery. The targeted location in the left renal vein is preferably the location spatially nearest to the superior junction between the left renal artery and the abdominal aorta.

The method utilizes an ablation catheter capable of ablating tissue using radio frequency energy at an electrode, laser energy, microwave energy, cryogenic cooling or ultrasound. If an rf electrode is used it may be irrigated so as to decrease damage to the endothelial cells lining the lumen of the renal artery preferably having a plurality of holes through which a cooling fluid is capable of flowing. The ablation catheter for ablating at the targeted location may have a plurality of spines each having an ablation element disposed at the distal end, such as "s" shaped spines curving into and then away from the longitudinal axis of the catheter. The spines may be made of nitinol and are designed to be substantially linear when constrained in a delivery sheath. The ablation catheter may incorporate a stabilizing member that is placed in a vessel near the target location so as to stabilize the ablation element. The stabilizing member may be an inflatable balloon and may be guided over a guidewire.

A further apparatus for the ablation of tissue at the target location in the abdominal aorta, inferior vena cava or left renal vein has an elongated tubular body having a distal tip with a plurality of spines disposed thereon wherein each spine has a free distal end and an ablation element disposed on the free distal end of each spine. The spines may support rf electrodes. The spines may be s-shaped curving toward and then away from the longitudinal axis of the elongated body. The spines may be made of a shape memory material, such as nitinol, that is capable of being substantially straight when constrained in a delivery sheath and which returns to the s-shape when no longer constrained in the delivery sheath. An additional apparatus for the ablation of tissue at a target location in the abdominal aorta, inferior vena cava or left renal vein in accordance with the present invention has an elongated tubular shaft having a proximal end and distal end, a distal assembly with a generally circular member disposed thereon, at least one ablation element disposed on the generally circular distal member and a control handle mounted at the proximal end of the elongated tubular shaft. The ablation element may be an rf electrode which may be irrigated.

The generally circular member includes a shape memory material, such as nitinol, to form the generally circular member when it is unconstrained. Such an apparatus may include a contraction wire extending through the elongated shaft and the distal assembly attached to the control handle including a first control member configured to actuate the contraction wire to contract the generally circular form. Such an apparatus may include a deflection wire extending through the elongated shaft, wherein the control handle includes a second control member configured to actuate the deflection wire to deflect a portion of the elongated body. The apparatus has at least one rf electrode, and preferably six ring electrodes, which may be connected to an electrical lead capable of providing signal indicative of a measure of temperature. The apparatus may include a plurality of location sensors, preferably, where the plurality of location sensors includes a distal sensor located near the distal end of the distal most electrode, a middle sensor located near an intermediate electrode and a proximal sensor near the distal tip of the distal assembly. The generally circular member may be an arc that subtends at least 180 degrees forming a semicircle when uncontracted which can be contracted into a smaller circular shape.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Currently renal denervation is performed within the renal artery and the optimum lesion set is a helically formed set of lesions within the renal artery that provides for a complete or nearly complete circumferential lesion around the artery, whether contiguously circumferential or not. Several alternative methods are described herein.

One method described herein is the use of ablation outside of the renal artery at the superior junction where the renal artery branches off from the aorta thereby focusing ablation energy where the nerves start following the path of the renal artery. At this junction point the nerves are dense and numerous. Denenervating the tissue at the location which includes a majority of this set of nerves using a single ablation interrupts the sympathetic nerve traffic. This method minimizes the number of ablation sites in the aorta therefore decreasing the chance of spasm or stenosis of the artery. By focusing on just one location of dense nerves the method also alleviates the need to create multiple ablation locations to try and target all the nerves. In this method it is necessary to ablate at the superior junction of the right and left renal artery.

The catheters for use in this method allows the user to direct the therapy at that site with a very stable position. The catheter is used to create a large and deep lesion so that all nerves at that location are denervated. The most advantageous method of energy delivery would be such that the energy delivery would be able to be focused deeper within the adventi tissue and spare as much of the endothelial layer as possible to avoid possible stenosis and also target the nerves in the adventitia as the targeted nerves are not at the surface or in the endothelia. Some known methods of energy delivery that have these characteristics are radiofrequency (RF) ablation catheters (irrigated or non-irrigated), focused ultrasound catheters or laser energy delivery catheters. Optimally the catheter would be able to sit around the renal artery and then ablate just at the juncture point. A balloon or a stabilizing member may be used as the anchoring device within the renal artery or a branch of a vessel to help locate and stabilize the point like ablation device which then is located to the side or forward of the anchoring device so that it is stabilized at the desired targeted junction location.

Figure 1:
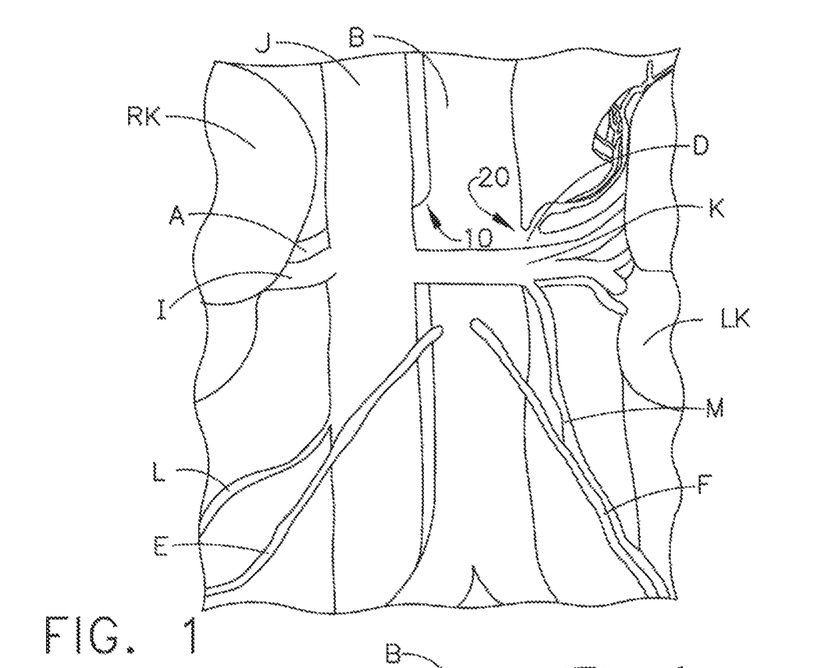
FIG. 1 is a diagram illustrating the abdominal anatomy of a human including the renal veins and arteries and depicting the ablation targets in accordance with a first method in accordance with the present invention.
Figure 2:
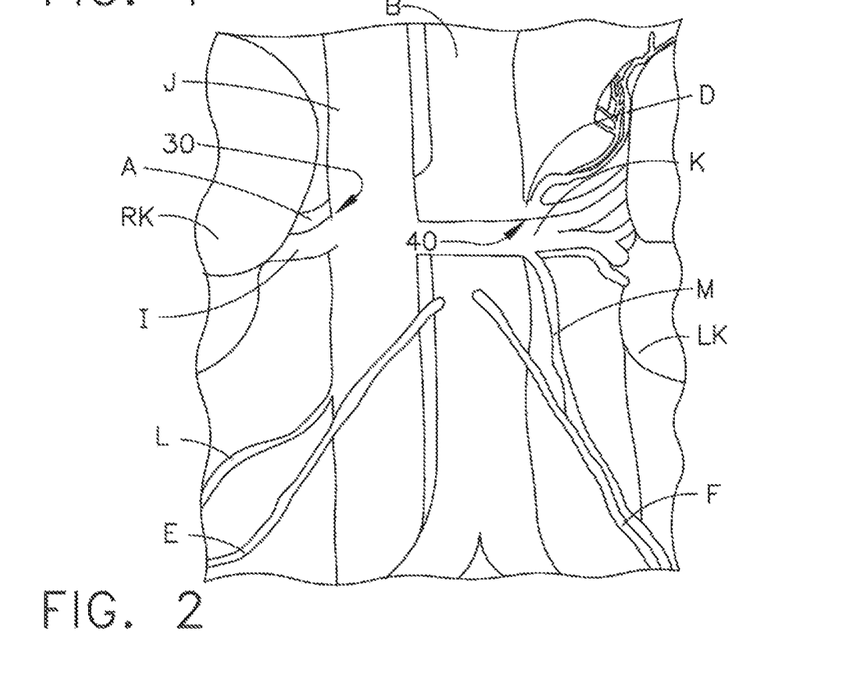
FIG. 2 is a diagram illustrating the abdominal anatomy of a human including the renal veins and arteries and depicting the ablation targets in accordance with a second method in accordance with the present invention.

FIG. 1 is a diagram showing the preferred locations for the targeted ablation of the renal sympathetic nerves in the right and left renal arteries. FIG. 2 is a diagram showing the preferred locations for the targeted ablation of the nerves of the right and left renal veins.

In FIG. 1, Left and right kidneys (LK and RK) are supplied with oxygenated blood by the right renal artery (A) and left renal arteries (D) which are in turn supplied by the abdominal aorta (B). Despite their relatively small size, the kidneys receive approximately 20% of the total oxygenated blood output of the heart. Each renal artery branches into segmental arteries, dividing further into interlobar arteries which penetrate the renal capsule and extend through the renal columns between the renal pyramids. Urine is excreted by the kidneys LK and RK then to the ureters and then to the bladder of the urinary system. Also shown in FIG. 1 are the right gonadal artery (E) and the left gonadal artery (F).

Once the oxygenated blood is used by the kidneys it flows from the kidneys back to the heart via the right renal vein (I) from the right kidney (RK) and via the left renal vein (K) from the left kidney (LK) through inferior vena cava or "IVC" (J). Also shown in FIG. 2 are the right gonadal vein (L) and the left gonadal vein (M). The kidneys and the central nervous system communicate via the renal plexus, whose fibers course along the renal arteries to reach each kidney. Renal nerves extend longitudinally along the length of and around the renal arteries RA generally within the adventitia of the wall of the artery approximately 3 mm below the endothelial layer.

FIG. 1 depicts the target locations for ablation in the abdominal aorta (B). A catheter is introduced into the abdominal aorta (B) and the ablation targets the nerves from the aorta side. Optimally the right bundle of nerves would be targeted and ablated at a single location in the abdominal aorta at the superior junction of the abdominal aorta where the respective right and left renal artery branches off at locations 10 for the right renal artery and 20 for the left renal artery respectively.

FIG. 2 depicts the target locations for ablation in an alternative embodiment of the present method targeting the location of dense nerves near the IVC (J). A catheter is introduced into the IVC and the ablation targets the appropriate nerves from the venous side. Optimally the right bundle of nerves would be targeted and ablated at a single location in the IVC at the junction of the IVC where the right renal vein branches (I) off from the IVC at 30. To target the left nerves the ablation is performed in the vicinity of a location in the left renal vein where the left renal artery branches from the abdominal aorta at the point where the left renal vein crossed over this branching junction 40. Ablation of the targeted nerves on the right side should occur at the location in the IVC that is nearest spatially to the superior junction between the right renal artery and the abdominal aorta. Likewise, ablation of the targeted nerves on the left side should occur at the location in the left renal vein that is nearest spatially to the superior junction between the left renal artery and the abdominal aorta. The ablation at these locations is meant to ablate through the wall of the IVC or left renal vein to target the nerves that enervate the right and left kidney but reside near the superior junction of the right and left renal arteries as they branch from the abdominal aorta.

In third embodiment of the method the ablation is performed at targeted locations inside the abdominal aorta at the ostia that lead to the right and left renal arteries or in the inferior vena cava at the ostia to the right and left renal veins.

Figures 3, 4:
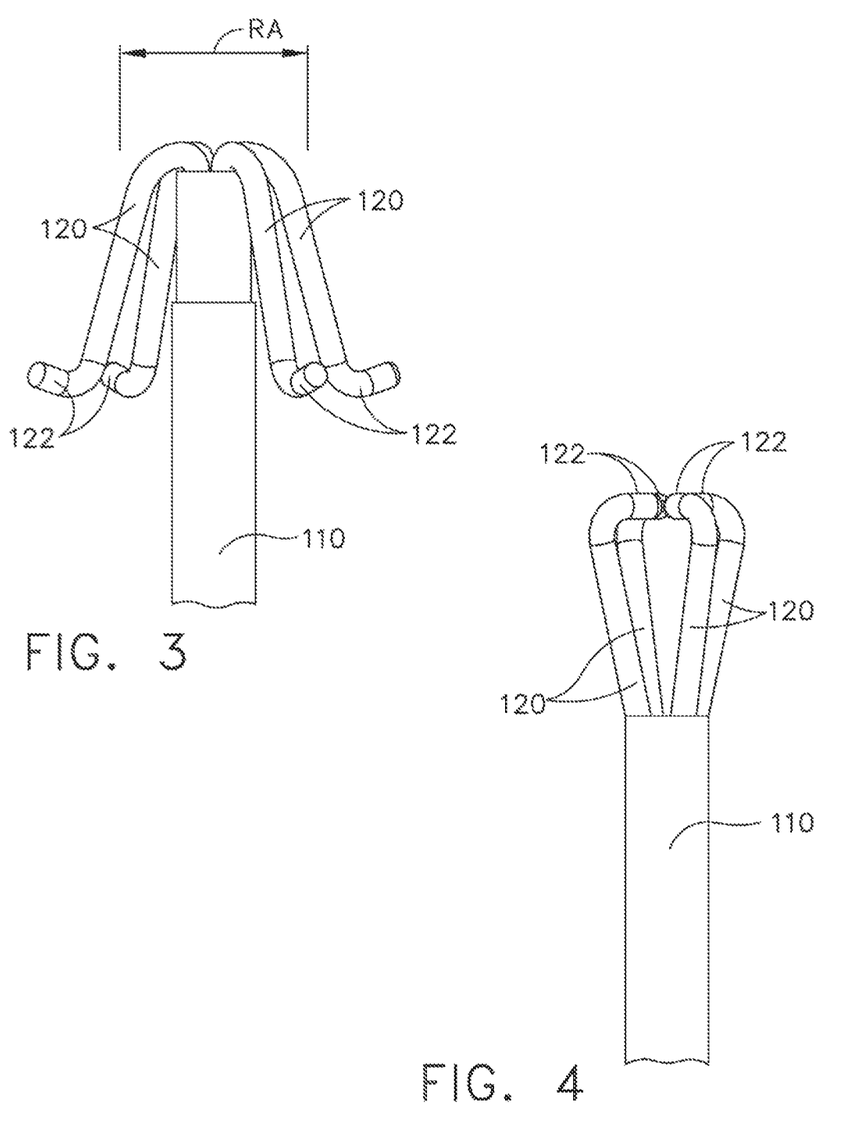
FIG. 3 is a side view of the distal section of an embodiment of a catheter for use in the method of the present invention and a depiction of its implementation at a targeted location.
FIG. 4 is a side view of the distal section of the catheter of FIG. 3 in a collapsed state for deployment within the veins or arteries.

FIG. 3 shows a catheter 110 designed to ablate at the ostium of a vessel such as, but not limited to, an artery or a vein. The particular embodiment describes a catheter that has a plurality of cantilevered spine assemblies at the distal end wherein each spine assembly has a free, unsupported distal end. The shape of the distal assembly is created from nitinol or other shape memory material. The shape of the distal structure in the free state position looks like multiple "S" shapes spines 120 protruding from the distal end of the catheter shaft. The ablation element 122 that sits at the distal end of the "S" shape forms the secondary curve. Due to the curve or elbow of the electrode, the electrode can engage the vessel's ostium. The Nitinol spines are covered by a Pebax, Pellethane or other thermoplastic elastomer.

When the catheter is retracted from the body the spines rotate almost a complete 180 degrees, which is directed by the guiding sheath or catheter. Due to the shape of the electrodes, when the spines are in their retracting position the distal assembly has an overall diameter that is the same or nearly the same as the diameter of the shaft. This feature permits the catheter to still be retracted through a sheath that is of clinically acceptable size. The retracted position of the catheter is depicted in FIG. 4.

If the ablation element 122 is an electrode it will have corresponding lead wires for energy application and temperature sensing. It is possible with this design to have electrodes that irrigate.

In a renal denervation procedure it may be critical to ablate the ostium of an artery where there may be high nerve density. Additionally, the catheter could be used in a procedure for the treatment of atrial fibrillation where it is desired to entrap the pulmonary veins by ablating around the ostium.

The advantages of the catheter of FIGS. 3 and 4 for use in the present method include the ability of a catheter/ablating electrode to conform to the ostium, the ability of the catheter to perform a single or multi-point ablation, the catheter can be used to ablate at the ostium and easily within a tubular vessel. Additionally, the catheter design is easy to retract into a guiding sheath/catheter and is designed to ensure that the catheter/ablating electrode engages the ostium.

Figure 5:
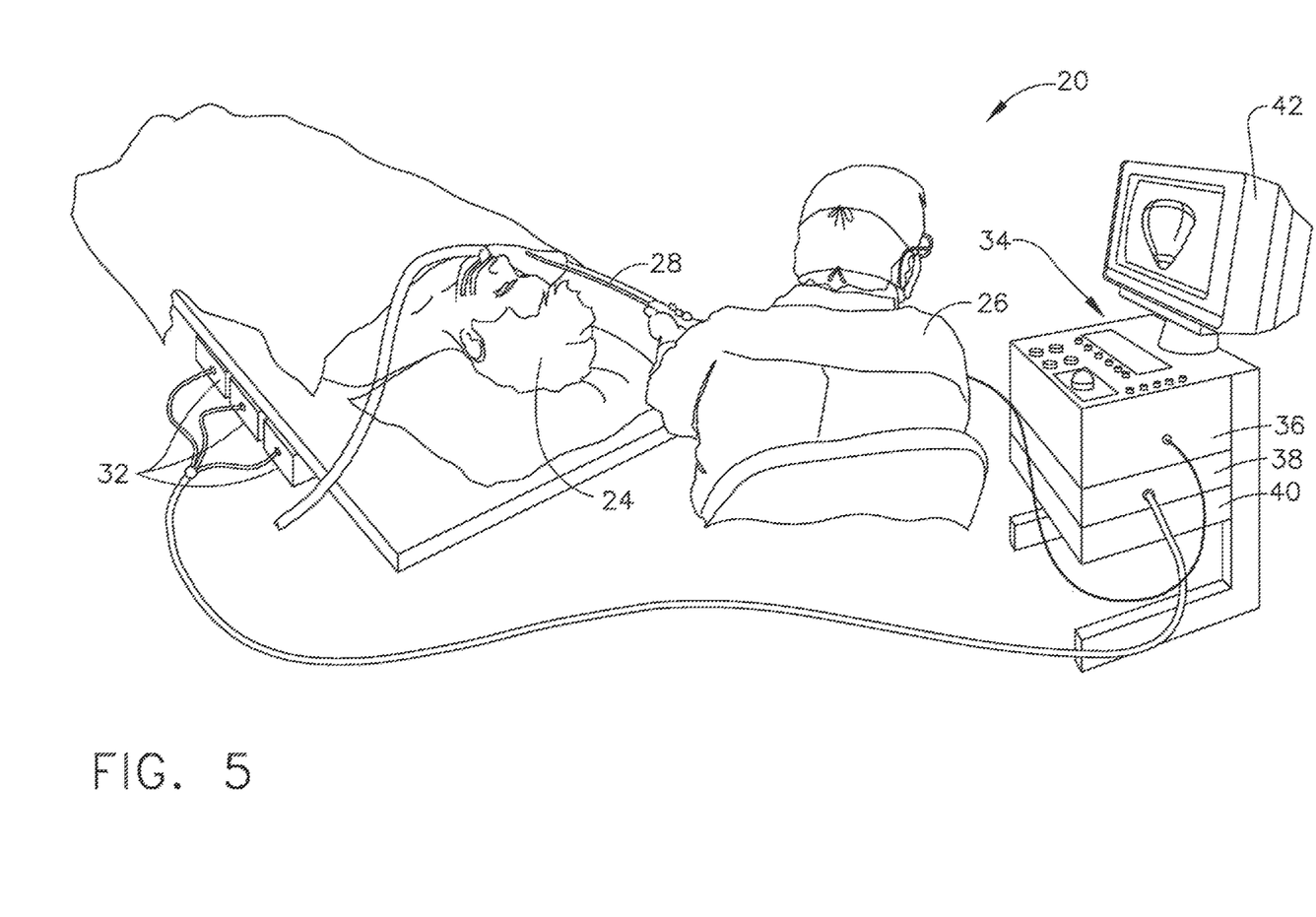
FIG. 5 is a schematic representation of a system for use in practicing the methods described herein.

FIG. 5 is a schematic, pictorial illustration of a system 20 for renal and/or cardiac catheterization and ablation, in accordance with an embodiment of the present invention. System 20 may be based, for example, on the CARTO™ system, produced by Biosense Webster Inc. (Diamond Bar, Calif.) and/or SmartAblate or nMarq RF generation system. This system comprises an invasive probe in the form of a catheter 28 and a control and/or ablation console 34. In the embodiment described hereinbelow, it is assumed that catheter 28 is used in ablating endocardial tissue, as is known in the art. Alternatively, the catheter may be used mutatis mutandis, for other therapeutic and/or diagnostic purposes in the heart, kidneys or in other body organs.

An operator 26, such as a cardiologist, electrophysiologist or interventional radiologist, inserts catheter 28 (which may be designed in accordance with FIG. 3 and or 4 or the later described embodiments below or comprise other known designs such as the Biosense ThermoCool or ThermoCool SF ablation catheter design) into and through the body of a patient 24 so that a distal end 30 of the catheter either enters the inferior vena cava or abdominal aorta or contacts the outside of the abdominal aorta. The operator advances the catheter so that the distal section of the catheter engages tissue at a desired location or locations described hereinabove. Catheter 28 is typically connected by a suitable connector at its proximal end to console 34. The console 34 comprises a radio frequency (RF) generator 40, which supplies high-frequency electrical energy via the catheter for ablating tissue in the heart at the locations engaged by the distal tip, as described further hereinbelow. Alternatively, the catheter and system may be configured to perform ablation by other techniques that are known in the art, such as cryo-ablation, ultrasound ablation or ablation through the use of microwave energy or laser light.

Console 34 may also use magnetic position sensing to determine position coordinates of distal end 30 inside the body of the patient 24. For this purpose, a driver circuit 38 in console 34 drives field generators 32 to generate magnetic fields within the body of patient 24. Typically, the field generators comprise coils, which are placed below the patient's torso at known positions external to the patient. These coils generate magnetic fields in a predefined working volume that contains the abdominal aorta near the renal veins and arteries. A magnetic field sensor within distal end 30 of catheter 28 (shown in FIG. 2) generates electrical signals in response to these magnetic fields. A signal processor 36 processes these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, now U.S. Pat. No. 6,690,963, 2003/0120150 A1, now U.S. Pat. No. 7,729,742, and 2004/0068178 A1, now abandoned, whose disclosures are all incorporated herein by reference.

Processor 36 typically comprises a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor 36 may be carried out by dedicated or programmable digital hardware components. Based on the signals received from the catheter and other components of system 20, processor 36 drives a display 42 to give operator 26 visual feedback regarding the position of distal end 30 in the patient's body, as well as status information and guidance regarding the procedure that is in progress.

Alternatively or additionally, system 20 may comprise an automated mechanism for maneuvering and operating catheter 28 within the body of patient 24. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 36 generates a control input for controlling the motion of the catheter based on the signals provided by the magnetic field sensor in the catheter. These signals are indicative of both the position of the distal end of the catheter and of force exerted on the distal end, as explained further hereinbelow.

Figures 6, 7:
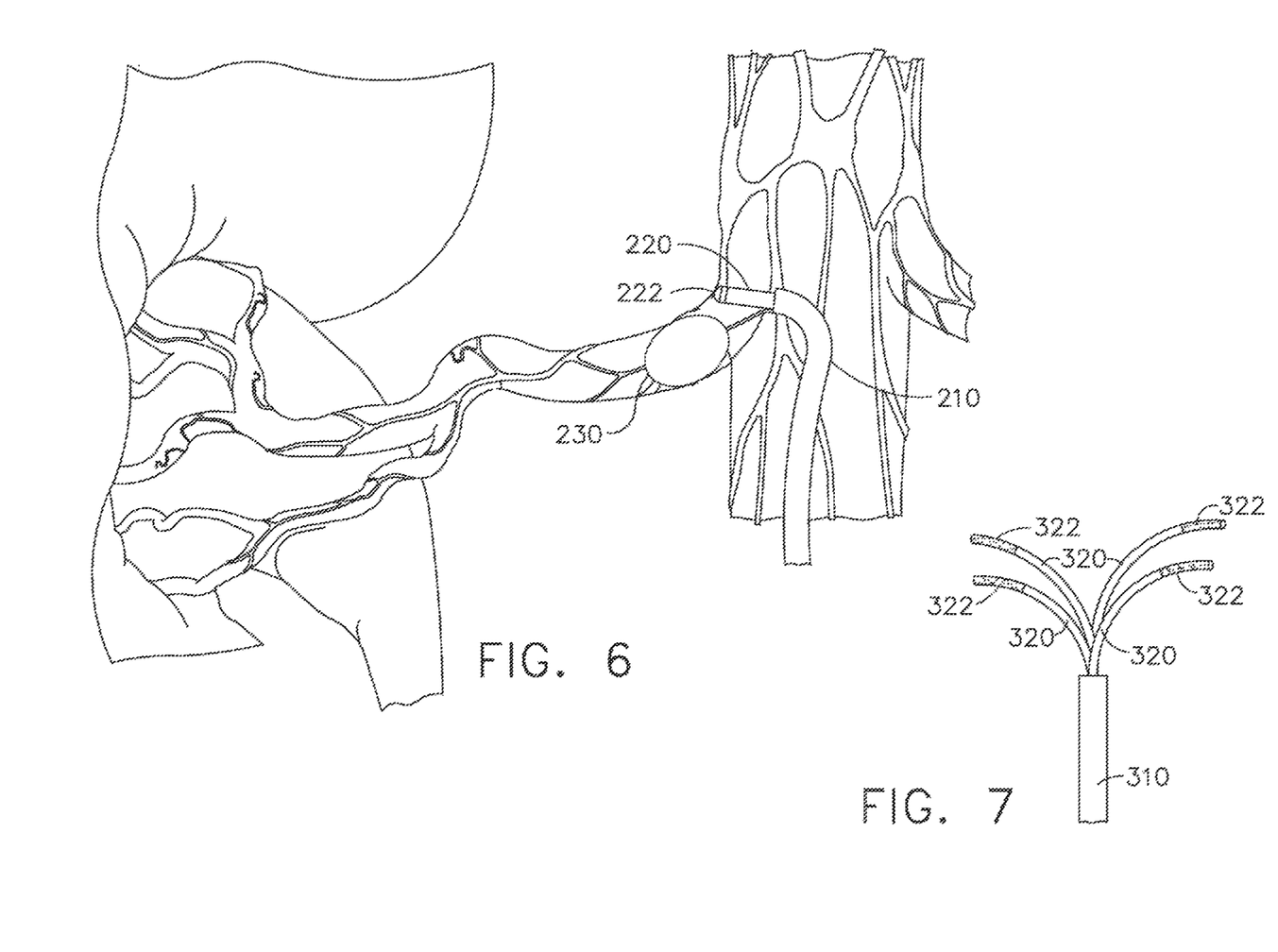
FIG. 6 is a diagram depicting a further embodiment of an apparatus for ablating the targeted location according to the present invention shown deployed in and near the renal artery.
FIG. 7 is a side view of a further embodiment of a catheter for use in accordance with the present invention.

FIG. 6 depicts a further embodiment of a catheter for use in the method of the present invention as deployed in the renal artery. In FIG. 6 an ablation electrode 222 on the distal tip of catheter 220 is used to make a point ablation at a target location. Catheter 220 is guided near the target location by guiding sheath 210. A stabilizing balloon 230 is anchored in the right renal artery (A) (or alternatively a renal vein) in order to stabilize the ablation electrode 222 at the target location. The stabilizing balloon 230 can be comprised of a polymer such as PET, nylon and polyurethane or similar materials. The stabilizing balloon is inflated with saline or similar fluid in order to provide an anchor in a vessel such as a renal artery or renal vein. Once the stabilizing balloon 230 is inflated the ablation electrode on the distal tip of catheter 210 is guided into contact with the point near the ostium where the ablation is targeted.

FIG. 7 is a side view of a further embodiment of a catheter for use in accordance with the present invention. Catheter 310 has a plurality of cantilevered, shape memory material arms or spines 320, each having a free distal end and each having one or more ablation electrodes 322 mounted at or near the distal end. The user may then chose to ablate using the electrode of the arm having the location closest to the target location, for example, closest to the plexus of nerves. Each tip has a tip electrode capable of delivering ablative energy to the targeted tissue. The arms 320 then may be retracted into a guiding sheath (not shown) which causes the arms to fold inward for withdrawal of the catheter 310 from the body of the patient.

Figure 8:
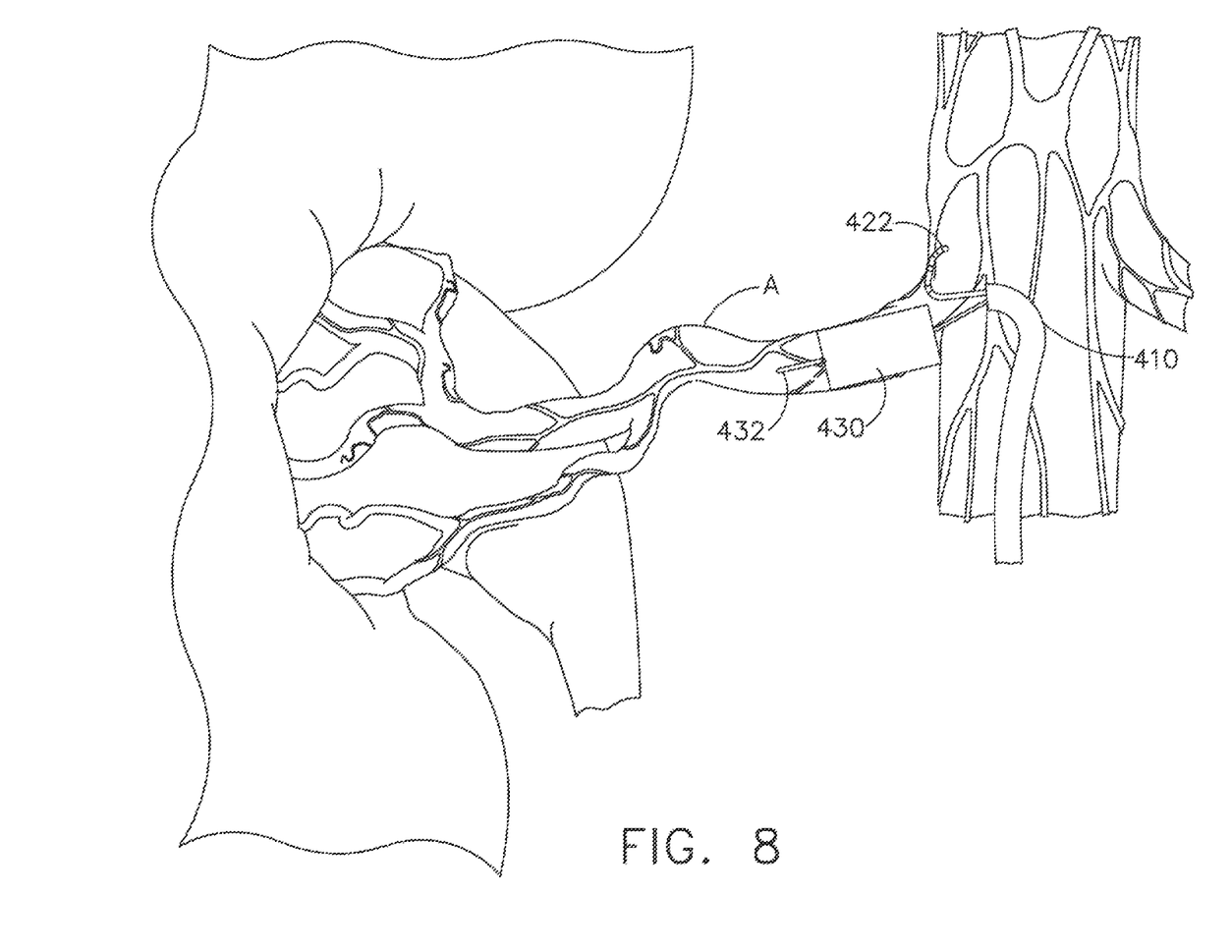
FIG. 8 is a diagram depicting a further embodiment an apparatus for ablating the targeted location according to the present invention shown deployed in and near the renal artery.

FIG. 8 is a diagram depicting a further embodiment of the invention deployed in and near the renal artery. Guiding sheath 410 is used to guide an ablation catheter 422 and a guidewire 432 that is guided distally of the guiding sheath 410 into the renal artery (or alternatively a renal vein). Ablation catheter 422 takes a rounded or "crescent" shape when unconstrained from guiding sheath 410 and contains one or more ring electrodes capable of delivering ablative energy to the target location. This would give the user the ability to determine the correct spot to ablate near the target location once the guidewire 432 and stabilizing member 430 are stabilized at the target location. Additionally rings electrodes could be placed on the stabilizing member to record energy signals to confirm whether electrical signals are still being transmitted to the renal artery (or other vessel). Stabilizing member 430 may be a balloon or other expandable member.

Figure 9A:
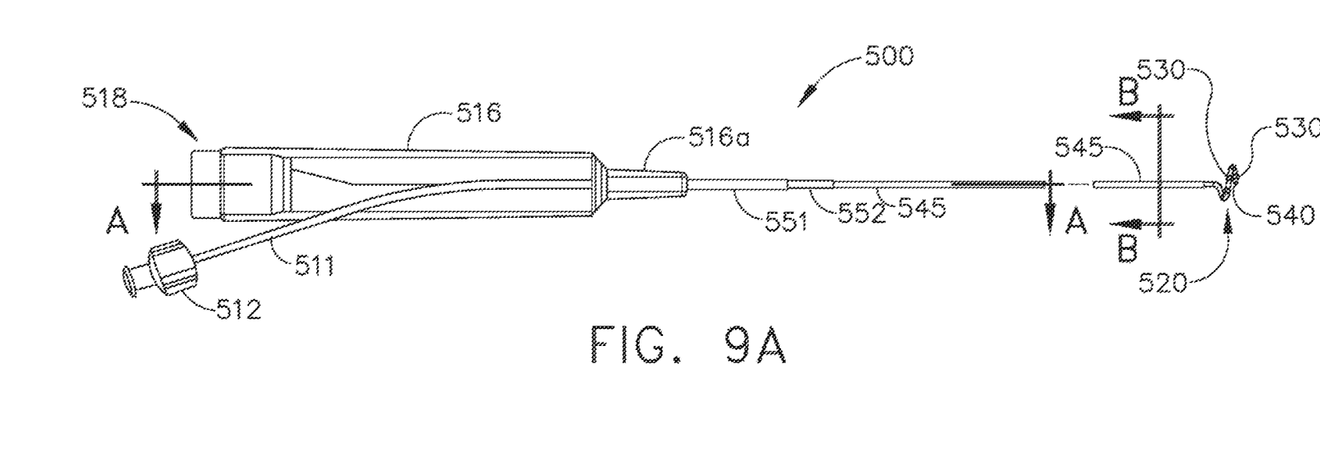
FIG. 9A is a side view of circular catheter 500 in accordance with and for use in the method of the present invention.
Figure 9B:
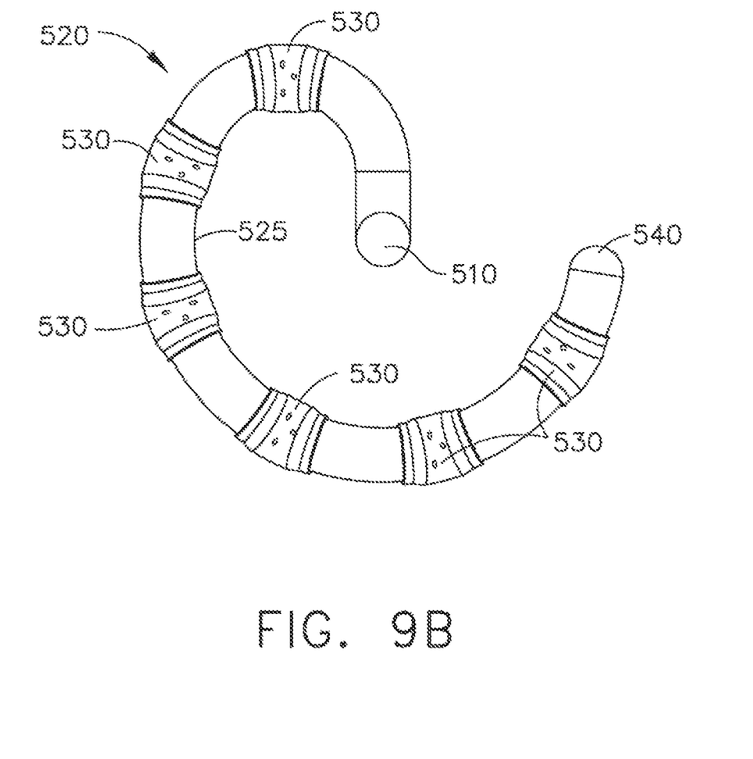
FIG. 9B is a bottom plan view of the distal end assembly of the circular catheter of FIG. 9A.
Figures 9C, 9D:
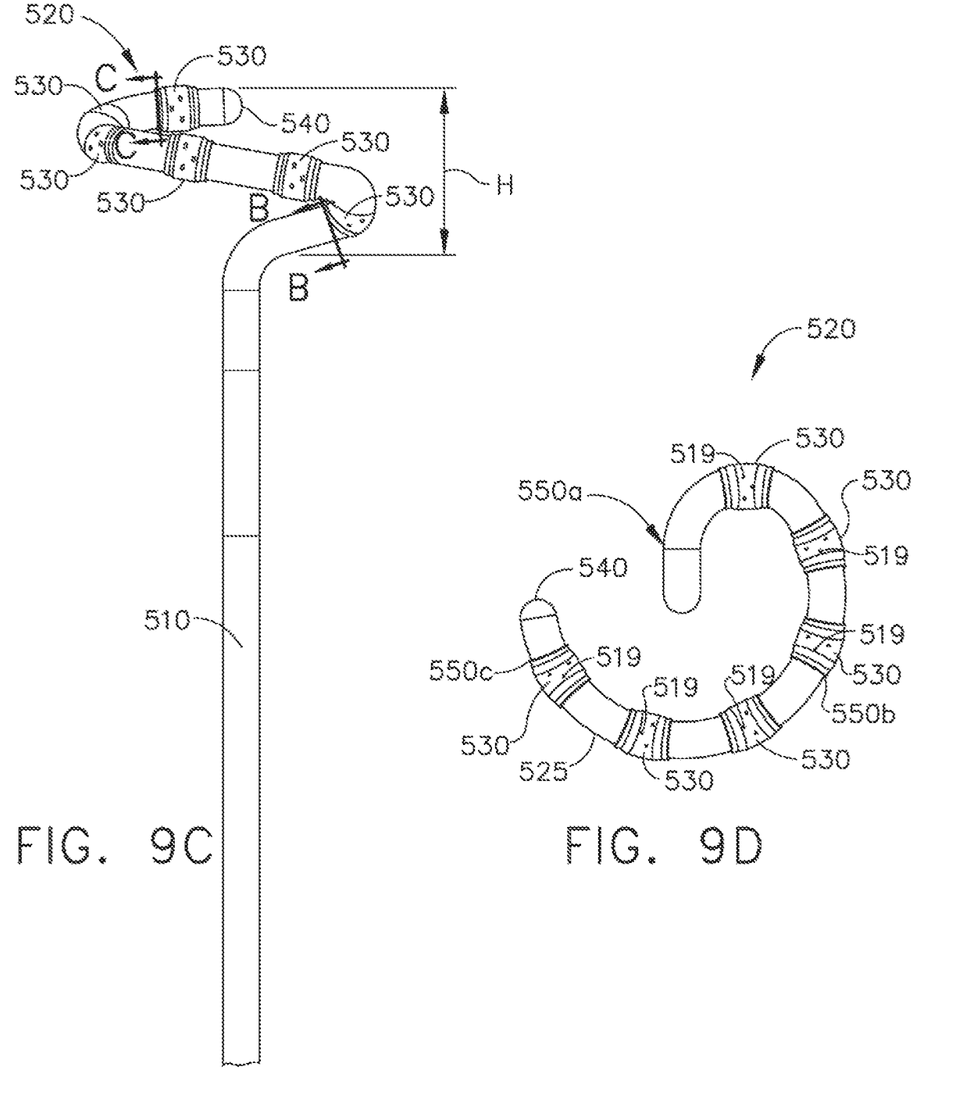
FIG. 9C is a side view of the distal end assembly and shaft of the circular catheter of FIG. 9A.
FIG. 9D is a top plan view of the distal end assembly of the circular catheter of FIG. 9A.

FIGS. 9A-H depict a catheter 500 that is designed for use in the method of the present invention. FIG. 9A is a side view of a catheter in accordance with the present invention. FIG. 9B is a bottom plan view of distal assembly 520 and FIG. 9C is a side plan view of the shaft 510 and the distal assembly 520. FIG. 9D is a top plan view of the distal assembly 520. Distal assembly 520 is a generally circular assembly with a height (H) of approximately 11 millimeters (mm). A plurality of ring electrodes 530, preferably six, is dispersed on the generally circular portion of the distal assembly. The distal most ring electrode 530 being approximately 3 mm from the atraumatic tip 540 which is preferably a polyurethane plug at the distal tip of the distal assembly 520. Each ring electrode is approximately 3 mm in length and is spaced from the next electrode by approximately 4 to 4.5 mm. Each ring electrode 530 is made of a noble metal, preferably a mixture of platinum and iridium although other noble metals such as gold and palladium may also be used, and is connected to a plurality of lead wires. Each ring electrode may be used for visualization, stimulation and ablation purposes. A thermocouple is attached to each ring electrode to provide an indication of the temperature at or near the tissue. RF energy can be delivered either individually to one electrode, simultaneously to more than one electrode or in a bi-polar mode between electrodes. The ring electrodes may be irrigated through a plurality of apertures (shown as 519 in FIG. 9D) connected to an irrigation lumen 535 and 535a described below.

The distal assembly also contains three sensors which may be three-axis magnetic location sensors or singles axis (SAS) sensors. A distal sensor 550c is located near the distal end of the distal most ring electrode 530. A middle sensor 550b is located near the distal end of the ring electrode 530 located near an intermediate or middle ring electrode. A proximal sensor is a "floating sensor" located near the atraumatic tip 540. The catheter 500 alternatively contains a contraction wire (not shown) that is used to vary the expansion and contraction of the loop to varying sizes. Such a contractible catheter could be made in two size ranges: one varying from between approximately 19 mm in diameter at the largest down to approximately 10 mm at its smallest fully contracted state; and a second smaller diameter catheter varying between approximately 14 mm in diameter at its largest down to approximately 6 mm at its smallest fully contracted state. If a contraction wire is not used the distal assembly 520 should be approximately 8 to 12 mm and preferably around 10 mm in diameter when unconstrained. The distal assembly 520 is designed to define an arc oriented obliquely relative to the axis and having a center of curvature on the axis. The term "oblique" in the present context means that the plane in space that best fits the arc is angles relative to the longitudinal axis of shaft 545. The angle between the plane and the axis is greater than 45 degrees. The arc subtends 180 degrees forming a semicircle which can then be contracted into a smaller circular shape. The angle of the subtended arc may vary from 90 degrees to 360 degrees, but in the preferable embodiment is 180 degrees.

The loop includes a base 510 which is connected to the distal end of the insertion shaft 545 and a tip. The loop features a centered, generally cylindrical form such that the tip protrudes axially in a distal direction relative to the base. Preferably, the axis of the base 510 and shaft 545 is centered along the diameter of the unconstrained loop, however, it may also be centered along the diameter of the constrained loop. The pitch of the distal assembly 520 is fixed along the length of the loop and is approximately 5 to 20 degrees.

The shape of the distal tip assembly arises by incorporating a structure made from a shape memory material such as nitinol which has been pre-formed to assume the desired shape when unconstrained at body temperature. The distal tip assembly is sufficiently flexible to permit the loop to straighten during insertion through a sheath (not shown) and then resume the arcuate form when unconstrained.

The shaft 545 of the catheter 500 is attached to a control handle 516 which has a narrower portion 516a at the proximal end of the shaft 545. Control handle 516 may alternatively include two independent mechanisms for controlling the expansion/contraction of the loop through a contraction wire and the deflection of the distal tip assembly using a puller wire as depicted in co-pending U.S. patent application Ser. No. 13/174,742 which is hereby incorporated by reference.

Catheter 500 may also incorporate a guidewire to ensure placement of the distal tip assembly at the proper location or it may incorporate a soft distal tip section parallel to the longitudinal axis of the shaft 545 and base 510 that would be used to guide the distal tip assembly into the proper location.

Figure 9E:
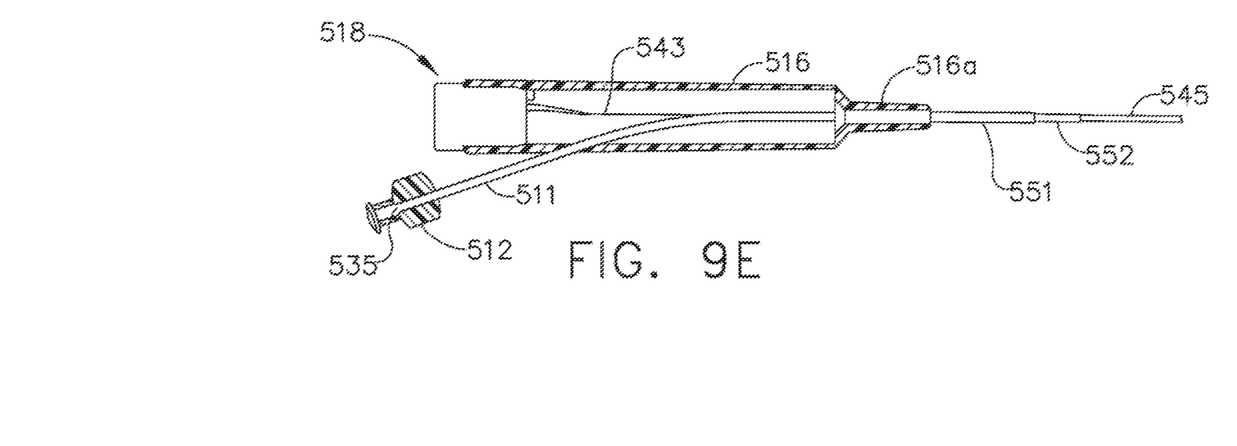
FIG. 9E is a cross-sectional view of a proximal portion of FIG. 9A through line A-A

FIG. 9A is a side view of catheter 500 in accordance with the present invention when no contraction or deflection wire is present. FIG. 9E is a cross-sectional view of the proximal portion of FIG. 9A through line A-A Control handle 516 is a generally cylindrical tubular structure but can also take other shapes and configurations that provide the user of the device with the ability to manipulate the catheter while providing an interior cavity for passage of components. Control handle 516 with narrower portion 516a is made of an injection molded polymer such as polyethylene, polycarbonate or ABS or other similar material. Connector 518 is inserted into the proximal end of control handle 516 and provides an electrical connection to a mating connector and cable assembly that is connected to an RF generator. Connector 518 is secured through the use of epoxy or other similar means. Lead wire assembly 543 comprises a Teflon sheath and six pairs of lead wires 541, 542 housed therein, one pair for each ring electrode 530 and associated thermocouple (not shown). The proximal end of each lead wire is electrically and mechanically connected to the connector 518 through the use of solder or other means. Irrigation luer hub 512 is a fitting capable of being attached to mating connector from an irrigation source such as an irrigation pump (not shown). Irrigation luer hub 512 is attached to irrigation side arm 511 using polyamide to form a seal against fluid intrusion. Irrigation fluid is then conveyed from the irrigation hub through the irrigation lumen 535. Irrigation lumen 535 passes through the lumen in side arm 511 through the wall of the control handle 516 through the shaft 545 and then into irrigation lumen 535a in the base 510 of the multi-lumen tube 525 for approximately 3 mm into the distal assembly 520 in order to convey irrigation fluid to each ring electrode 530 which has a plurality of holes apertures 519 therethrough as depicted in FIG. 9D. The catheter 500 may also be constructed without irrigation.

Control handle 516 has a portion which of a smaller diameter 516a which is adapted to receive the proximal end of the catheter assembly 570 which is comprised of strain relief element 551, 552 and shaft 545 through which lead wire assembly 543 and irrigation lumen 535 pass. Strain relief elements 551 and 552 in the preferred embodiment are two shrink sleeves made of polyolefin or similar material which are heated to shrink over the shaft 545. Polyurethane is then used to attach the strain relief elements 551 and 552 into the handle portion 516a.

The working length (L) of the catheter assembly 550 is approximately 90 cm from the distal end of strain relief element 552 to the distal tip of the distal assembly 520 when used for renal ablation. The working length may vary depending on the application. Distal assembly 520 comprises a multi-lumen tube 525 which has a plurality of ring electrodes 530 mounted thereon. In a preferred embodiment for renal ablation six ring electrodes are used. The maximum diameter of the generally circular distal assembly 520 is approximately 8-12 mm, preferably around 10 mm when un-constricted. The ring electrodes 530 preferably have a maximum outer diameter of 2 mm at the middle and a minimum outer diameter of 1.7 mm at the narrower ends. The ring electrodes may be made on any material described herein but are preferably made of 90% platinum and 10% iridium but cold be comprised a combination of these and/or other suitable noble metals such as gold and palladium. Multi-lumen tube 525 with base 510 are made of a material that is more flexible than the material in the shaft 545 preferably 35D PEBAX with no wire braid, although other materials and durometers may be used depending on the desired stiffness of the distal assembly 520. Shaft 545 is made of pellethane, polyurethane or PEBAX and contains an internal stiffener, as described herein, which is an inner tube made of nylon or polyimide or similar material.

Figure 9F:
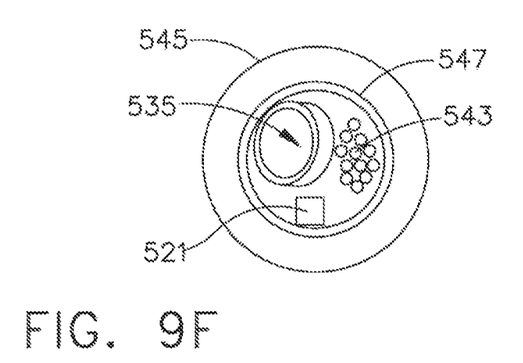
FIG. 9F is a cross-sectional view of the catheter of FIG. 9A through line B-B.
Figure 9G:
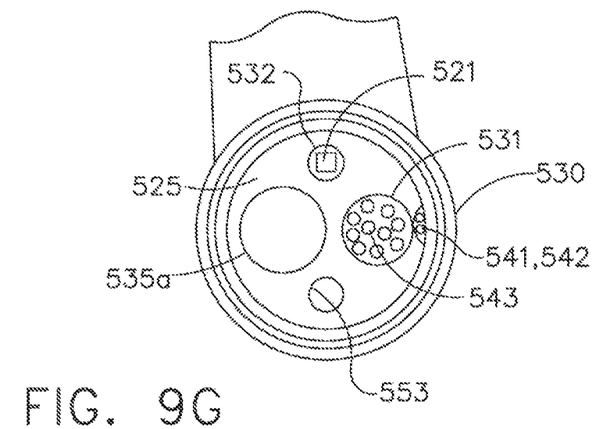
FIG. 9G is a cross-sectional view of the distal assembly of FIG. 9C through line C-C.
Figure 9H:
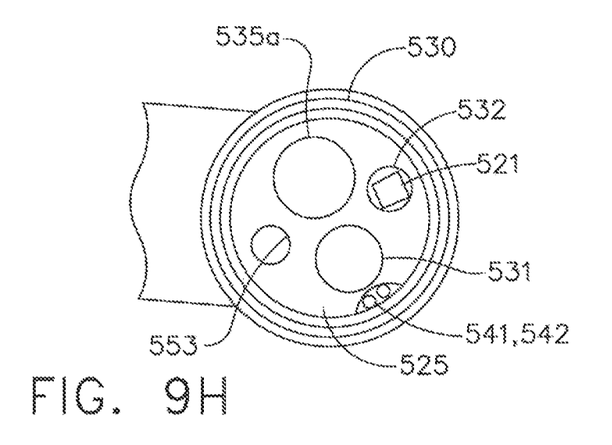
FIG. 9H is a cross-sectional view of the distal assembly of FIG. 9C through line D-D.

FIGS. 9B-H show a portion of the distal assembly 520 containing the ring electrodes 530. Each pair of lead wires 541 and 542 is welded to a respective ring electrode to provide a robust connection. A polyurethane coating is placed over each end of each ring electrode in order to seal against a fluid intrusion and to provide an atraumatic transition between the electrodes 530 and the multi-lumen tube 525 of distal assembly 520. FIGS. 9F-9H show the distal assembly 520 connected to shaft 545 and various cross-sections therethrough. FIG. 9F is a cross-sectional view of FIG. 9A through B-B in shaft 545. FIG. 9G is a cross-sectional view of FIG. 9C though line C-C. FIG. 9H is a cross-sectional view of FIG. 9C through line D-D. Atraumatic tip dome 540 is a polyurethane dome with a shaft that extends into the end of the irrigation lumen 535a at the end of the multi-lumen tube 525. The nitinol wire/shape memory support member 521 extends from at or near the distal end of the multi-lumen tube 525 into the shaft 545 for approximately 25 millimeters into the shaft. This provides stability to the distal assembly 520. Nitinol wire 521 is preferably square in cross-section 0.0075 inch by 0.0075 inch) but could be square, circular or rectangular in cross-section with a width or diameter between 0.006 inch and 0.010 inch. The nitinol wire is pre-formed to take a generally circular shape having a diameter of approximately 10 mm and a height H of approximately 5 to 11 preferably approximately 7 when it is in not constrained within a sheath. The nitinol wire will impart this circular shape on the other components of distal assembly 520. In FIGS. 9G and 9H the cross-sections of multi-lumen tube 525 shows ring electrode 530 mounted on multi-lumen tube 525. Multi-lumen tube 525 also contains an irrigation lumen 535a and a lead wire lumen 531 housing the lead wire assembly 543 which comprises pairs of lead wires 541 and 542. In FIG. 9G the connection of a first pair of lead wires (541, 542) that is connected to electrode 530 is shown. The additional pairs of lead wires can be seen in the remainder of lead wire assembly 543 in FIG. 9G. FIG. 9H shows the final pair of lead wires (541, 542) which will be attached to the distal most electrode 530. Lumen 532 houses the nitinol wire 521. Lumen 553 is in multi-lumen tube 525 is unused in the preferred embodiment but could be used for a contraction wire, wiring for additional thermocouples or other sensors that are desired in the tip assembly. In FIG. 9F the arrangement of the nitinol wire 521, irrigation lumen 535 and the lead wire assembly 543 within the shaft 545 can be seen. Stiffener 547 provides added stiffness to the shaft 545 and is comprised of a material such as polyimide or nylon, preferably polyimide having a thickness of approximately 0.002 thousandths. The stiffener 547 runs substantially the entire length of the shaft 545. Polyurethane is used to bond shaft 145 to the base 510 of the multi-lumen tube 525. This preferred polyurethane bond prevents fluids from entering at the junction of these two elements. Other methods of bonding such as heat sealing or other glues may be used.

Additionally, a fluoro-opaque marker may be placed at or near the distal end of the distal assembly 520 to aid visualization under fluroscopy. Such a fluoro-opaque marker can be a ring shaped structure made from a noble metal such as a combination of platinum and iridium of a similar composition to a ring electrode 19, however such a marker band may be narrower in width and would not contain apertures for irrigation fluid.

In use, the catheter assembly 500 is used with a sheath, preferably, a steerable sheath (not shown) which facilitates the placement of the catheter in the proper place in the anatomy for the desired ablation/denervation. Once the distal end of the catheter assembly 550 exits the sheath the nitinol wire/support member 521 will cause the distal assembly to take the pre-configured generally circular shape. The generally circular shape will provide sufficient apposition of the ring electrodes against the interior wall of the aorta or IVC at the target locations described above a the superior junction near or around the ostia to a renal artery or vein to provide contact for an ablation that upon the delivery of RF energy from a generator to one or more of the ring electrodes will result in the denervation or partial denervation of the renal artery.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. In that regard, the foregoing description should not be read as pertaining only to the precise structures described and illustrated in the accompanying drawings, but rather should be read consistent with and as support to the following claims which are to have their fullest and fair scope.

What is claimed is:

1. A method for the treatment of a patient comprising the steps of:
   inserting an ablation catheter into the inferior vena cava of a patient; and
   ablating tissue at a targeted location in the inferior vena cava in the vicinity of where the right renal vein branches off from the inferior vena cava so as to denervate the renal artery.

2. The method of claim 1 wherein the target location is in the vicinity of the ostium of the inferior vena cava and the right renal vein.

3. The method of claim 1 wherein the targeted location in the inferior vena cava is the location spatially nearest to the superior junction between the right renal artery and the abdominal aorta.

4. An apparatus for the ablation of tissue at a target location in the abdominal aorta, inferior vena cava and/or left renal vein comprising:

an elongated tubular shaft having a proximal end and distal end;

a distal assembly with a generally circular member disposed thereon;

at least one ablation element disposed on the generally circular distal member;

and a control handle mounted at the proximal end of the elongated tubular shaft.

5. The apparatus of claim 4 wherein the ablation element is an rf electrode.

6. The apparatus of claim 5 wherein the rf electrode is irrigated.

7. The apparatus of claim 4 wherein the generally circular member further comprises a shape memory material to form the generally circular member when it is unconstrained.

8. The apparatus of claim 7 wherein the shape memory material is nitinol.

9. The apparatus of claim 4 further comprising a contraction wire extending through the elongated shaft and the distal assembly, wherein the control handle includes a first control member configured to actuate the contraction wire to contract the generally circular form.

10. The apparatus of claim 4 further comprising a deflection wire extending through the elongated shaft, wherein the control handle includes a second control member configured to actuate the deflection wire to deflect a portion of the elongated body.

11. The apparatus of claim 4 wherein the at least one rf electrode is connected to an electrical lead capable of providing signal indicative of a measure of temperature.

12. The apparatus of claim 4 wherein the rf electrodes comprise six ring electrodes.

13. The apparatus of claim 4 wherein the distal assembly comprises a plurality of location sensors.

14. The apparatus of claim 13 wherein the plurality of location sensors includes a distal sensor located near the distal end of the distal most electrode, a middle sensor located near an intermediate electrode and a proximal sensor near the distal tip of the distal assembly.

15. The apparatus of claim 14 wherein the generally circular member is an arc that subtends at least 180 degrees forming a semicircle when uncontracted which can be contracted into a smaller circular shape.

* * * * *